United States Patent [19]

Kummer

[11] 4,092,246
[45] May 30, 1978

[54] HELICALLY WOUND BLOOD FILTER

[75] Inventor: Frederick J. Kummer, Boston, Mass.

[73] Assignee: Abcor, Inc., Wilmington, Mass.

[21] Appl. No.: 798,666

[22] Filed: May 19, 1977

Related U.S. Application Data

[63] Continuation of Ser. No. 578,330, May 16, 1975, abandoned.

[51] Int. Cl.² .............................................. B01D 37/00
[52] U.S. Cl. ........................................ 210/65; 55/477; 55/520; 55/524; 128/214R; 210/494 R; 210/497.1; 210/504; 210/505; 210/508; 210/DIG. 23
[58] Field of Search ...................... 210/497, 497.1, 65, 210/504, 505, 446, 448, 500, 503, DIG. 23, 494 R, 508; 55/520, 477, 486, 487, 503, 504, 524; 128/214 R, 214 C, 214 Z

[56] References Cited

U.S. PATENT DOCUMENTS

| 1,700,126 | 1/1929 | Goodloe | 55/524 |
| 2,425,235 | 8/1947 | Ferrante | 55/524 |
| 2,782,933 | 2/1957 | Monsarrat | 210/504 |
| 3,888,250 | 6/1975 | Hill | 210/DIG. 23 |

Primary Examiner—Frank Sever
Attorney, Agent, or Firm—Richard P. Crowley

[57] ABSTRACT

A filter for the filtration of blood characterized by a high flow rate with low pressure drop, which filter comprises: a filter housing; an inlet in the housing for the introduction of the blood to be filtered; an outlet in the housing for the removal of filtered blood; and a filter element disposed within the housing, which element comprises a helically coiled strip of sheet material containing a surface layer of fibrous flocked material on at least one side thereof, the sheet material wound into a helical coil of desired tightness, and the flocked material selected to remove particles from the blood to be filtered.

39 Claims, 5 Drawing Figures

U.S.Patent May 30, 1978 4,092,246

HELICALLY WOUND BLOOD FILTER

This is a continuation of application Ser. No. 578,330, filed May 16, 1975 now abandoned.

BACKGROUND OF THE INVENTION

Filters for the filtration of blood are used in transfusion, extracorporeal circulation and dialysis to remove debris and microemboli from the blood. These filtrants can deliteriously affect these external systems by clogging and more critically compromising the safety of the patient if introduced into his blood. Since conventional screen filters (170 to 200$\mu$) do not remove these aggregates of blood components, more elaborate filters have been developed to deal with this problem. Currently, there are three types of such filters in use; to wit, a Dacron wool filter (Swank); a polyurethane foam filter (Bentley); and a polyester mesh filter (Pall). The Swank and Bentley filters are both constructed in depth as to yield a large filtering and adhesive surface area comprised of interstices within the filter material (the size of which gradually decreases to less than 27$\mu$ for the polyurethane foam). The polyester mesh filter is a single-layer, woven screen of about 40$\mu$ pore size, pleated to obtain a large surface area.

Various studies have examined and evaluated one or more of these filters on the following bases: a) screen filtration pressure (SFP) post filter (the pressure required to force blood at a constant rate through a single filter with 20$\mu$ pores); b) pressure drop across filters; c) analysis of particle, leukocyte, platelet counts and blood chemistry before and after filtration; d) changes of oxygen partial pressure in patients with and without filtration; e) counting of microemboli by means of ultrasonic techniques and by utilizing a Coulter thrombocounter; and f) clinical studies of patient responses. Unfortunately, this data is not conclusive, nor were all tests run on each of the three filters. Certain of these tests suffer from intrinsic error and thus resulting experimental observations are not directly a manifestation of filter efficacy and can be misleading. For example, SFP is not only a function of microemboli buildup, but can also arise from thrombus formation on the screen itself. The Swank filter removes cellular microemboli effectively, but does not affect fat emboli which can account for 80% of the total emboli. Further associated problems with these prior art filters are: a) that they tend to clog with use, restricting flow and causing hemolysis; b) that they remove platelets and, therefore, alter blood coagulation-regulatory mechanisms; c) that changes in flow velocity can affect filtering action; and d) that the filters possibly introduce polymer fibers into the blood.

A filter for the filtration of blood should desirably exhibit certain properties. First, microemboli and foreign matter of all sizes must be effectively removed from the blood without changing the properties of the blood; i.e., removal of red blood cells, leukocytes and platelets or causing hemolysis. Secondly, the filter should have a low pressure drop which would remain constant as a function of time. Flow rates of up to 6 liters a minute must be at low pressure drops with effective filtration, and the filter must remain stable during pressure changes. Thirdly, a low-priming volume of blood or a means of removing entrapped air is required. Fourthly, the filter materials should not react deliteriously with the blood (i.e., cause thrombosis), nor should material, such as fibers, be introduced into the blood.

SUMMARY OF THE INVENTION

My invention concerns an improved filter and a method of filtration, and in particular relates to a coil-type filter useful for the filtration of blood and a method of filtering blood. More particularly, my invention is directed to an improved filter which is characterized by the use of a helical coil-type filter element comprising a sheet material and containing a flocked material on at least one surface thereof, and wherein the fluid stream to be filtered is passed axially through the helical coil filter element, thereby providing filtration with a high flow rate and a low pressure drop.

My filter comprises a filter housing adapted to contain a filter element, a filter element disposed in the filter housing and which comprises a helically coiled strip of sheet material having on at least one surface, but preferably two surfaces, thereof flocked material, such as fine fibrous flocked material, having a relatively short length for blood filtration, as hereinafter set forth, and an inlet in the housing for the introduction of a fluid stream, such as blood, to be filtered, and an outlet in the housing for removal of the filtered stream after passage through the filter element.

In the preferred embodiment described more particularly hereinafter, and for the filtration of blood, the inlet is generally disposed within the housing to permit the introduction of the fluid stream to be filtered axially of the helically coiled filter element, and even more preferably, the fluid stream to be filtered should be distributed uniformly by the use of a flow distributor across the cross-sectional area of the helically coiled filter element prior to introduction into the element and filtration. My filter is economical to manufacture and is simple in design and construction, and yet permits efficient filtration at high flow rates and low pressure drops, particularly when used in the filtration of blood. My filter permits filtration by screen filtration, depth filtration and absorption, adsorption. Treatment of the flock by chemical or physical means can effect a selective contaminate removal by reaction, complexing or chelation.

My filter permits low pressure drops at high flow rates, since the area and openings of the filter element do not change as a function of the flow rates. Further, by control of the length, diameter and density (# flock/area) of the fibrous flocked material and through the tightness of the helical winding, the particle size of the material to be removed in the fluid stream can be simply and easily controlled. Furthermore, my filter permits the surface of the flocked material to be modified or altered, such as by chemical treatment or reagents, to reduce the removal of leukocytes and platelets, and to promote the removal of emboli or to remove other particles or contaminates in other streams to be filtered. The flocked material may be treated, modified or a particular material selected to accomplish the desired removal; for example, the selection of a proper polymer, such as nylon, to remove white blood cells, or the selection of polyester flocked material to remove platelets, or a mixture of any combination thereof to remove selected particles or biological constituents of the blood stream or other body streams, or any fluid stream.

My filter permits a large surface area due to the flocked material, so that there are numerous channels presented in the filter element, so that occlusion of the filter element will be very slow, while changes in pressure will not disrupt filtration. In addition, my filter may be made of a small size, so that the priming volume where blood is involved is quite low, and the air can be easily removed from the outlet if desired through an air outlet opening in the upper filter housing. Thus, the coiled filter element provides for a flocked material with numerous small channels to remove physically particles in the fluid stream by entrapment in a large surface area of the flocked elements in the helical coil for selective adsorption or absorption of particles from the fluid stream.

The filtration efficiency can also be modified by variation, such as in the nature of the flocked material, the dimensions of the flocked material and the tightness of the winding employed within the fixed housing, so as to permit the filter not only to have utility in the filtration, but for the filtration of a wide variety of other liquid and gaseous streams.

For the purposes of illustration only, my filter will be described in connection with the design for the filtration of blood. However, it is recognized that various changes and modifications may be made in the filter, and that a wide variety of fluid streams can be filtered employing my filter.

DESCRIPTION OF THE EMBODIMENTS

Figure 1:
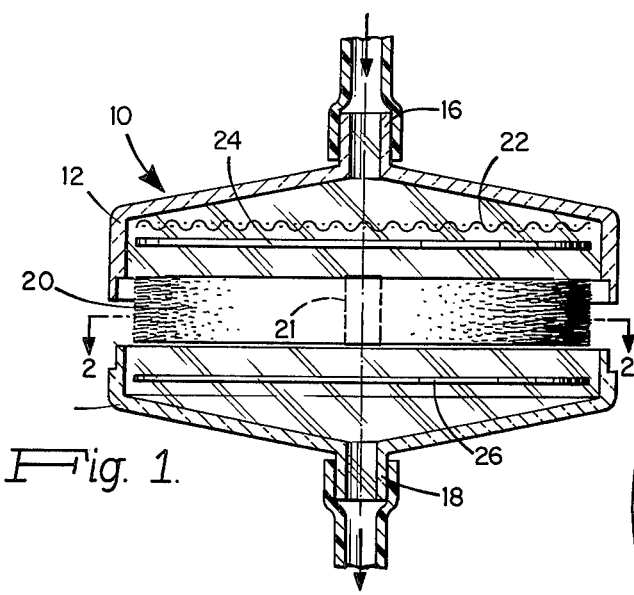
FIG. 1 is a partially exploded, partially schematic illustrative view of my filter.
Figure 2:
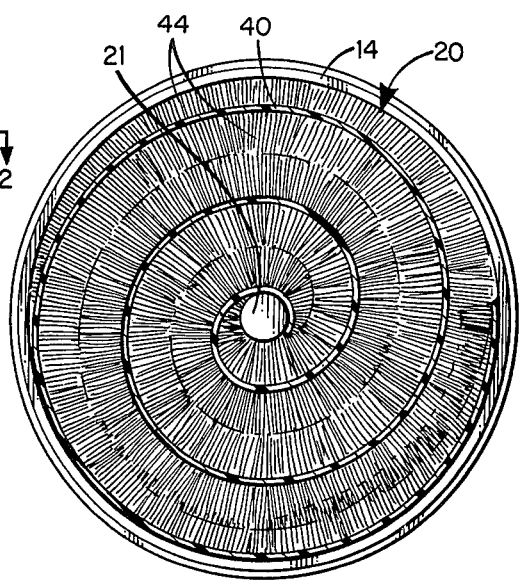
FIG. 2 is a cross-sectional view of FIG. 1 along lines 2—2 of FIG. 1.

FIG. 1 shows my filter 10 comprising a funnel-like upper housing 12 and a lower housing 14 which are adapted to be matingly engaged to form a closed filter housing having a centrally disposed upper inlet 16 and a centrally disposed lower outlet 18. Preferably, the filter housing elements are formed of a nonthrombogenic, easily formed, economical material, such as a polymeric material, such as a polycarbonate, polypropylene, polyethylene or the like. Disposed within the filter 10 is a helically coiled filter element 20 which comprises, as illustrated more particularly in FIG. 2, a sheet material 40, and preferably both surfaces thereof covered with a finely divided, fibrous, flocked material 44 which is secured to the sheet material 40 through an adhesive layer 42. The sheet material 40 serves as a backing, and typically should be composed of a thin stiff material which provides a good adhesion for any adhesive layer, and may be composed of a polymeric nonporous material, such as a polyester sheet material, from 0.5 to 5 mils. The adhesive layer is formed from any adhesive-type material which should be inert to the blood to be filtered or other material to be filtered, and typically is composed of well-known adhesive materials, such as solvent-based urethane, medical grade type A silicone rubber, vinyl-resin solvent-based material or other adhesive material which may provide for chemical inertness.

The size, length and distribution of the flocked material 44 to be employed may be varied at filtering characteristics of the filter. In a blood filter, the flocked material selected must be compatible with the blood, and should be somewhat stiff to adhere well to the adhesive layer 42. Typically materials which may be employed in a blood filter would include, but not be limited to: fibrous inert polymeric materials, such as polyamide material like nylon, polyester materials, cellulose ethers and esters like cellulose acetate, urethane foam material, as well as other natural and synthetic fibrous materials, such as other foam particles, cotton, wool, dacron, rayon, acrylates and the like. Preferably, in a blood filter, the length of the flocked material should not typically exceed about 1 to 3 mm, or preferably about 1.5 mm in length. The flocked material is precision-cut so that all fibers are of the same length, although a longer material may be used in filtering other types of streams if desired. In blood filters, if the flocked material is too long, the flocked material can compact at high flow rates, and, therefore, be less efficient. The nature of the flocked material to be selected is such that the flocked material may remove particular components from the fluid stream, such as in a blood filter, the flocked material is preferably a polyester, such as a 40 mil 3 denier natural polyester.

The spiral wound filter element 20 is formed into a helical core, and in one preferred embodiment, is formed about a solid inert polymeric core element 21, wherein the one end is glued to the core element, and then the filter element wound about this core to the desired tightness. The length of the sheet material determines the winding tension as the external diameter of the housing side is fixed. For example, where the housing is about 2¼ inches wide for a blood filter, the length of the spiral would be about 100 cm, wherein a 2 mm nylon flock is used as the material, and the sheet backing material is a 3 mil mylar polyester film. The width of the filter element 20 from top to bottom effects the pressure drop, and typically in a blood filter as described with from 1.0 to 2.0 cm used.

As illustrated in FIG. 1, a screen element 22 is employed in the housing, together with a flow distributor 24 and a post filter 26 in the lower part of the filters 22 and 26. The flow distributor 24 should be composed of a material similar in material as the filter housing. The screen filter 22 may be a polymeric screen formed of polyester and typically have a pore size of from about 50 to 200 microns. The filter 26 employed downstream of the stream to be filtered is designed in blood filtration to catch any flocked material 44, in the event that any such material becomes detached from the filter element 20. The filter 26 should be of such size to catch such flocked material based on the flocked material size employed.

Figure 3:
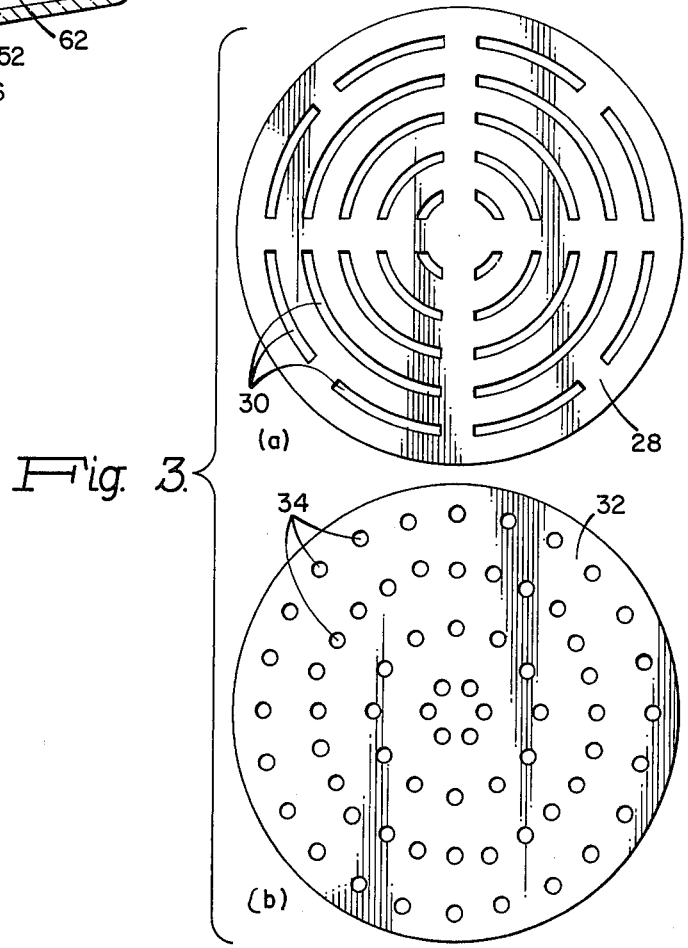
FIGS. 3a and 3b are representative plane views of flow distributors employed in the filter of FIG. 1.

The flow distributors, which are illustrated in FIGS. 3a and 3b, are employed to distribute the blood stream from the inlet uniformly across the cross-sectional diameter of the filter prior to introducing the stream axially through the filter element 20. Such flow distributors are designed to equalize the flow uniformly across the filter element, and typically may be employed by various distributions of holes and slots in a flow distributor. Typical flow distributors are illustrated more particularly in FIG. 3a, wherein there is shown a flow distributor 28 having a series of peripheral slots 30, and in FIG. 3b of another flow distributor 32 composed of a sieve plate having a plurality of holes 34 therein. The filters 22 and 24 and flow distributor 26, while desirable in the use of a blood filter, are not wholly essential, and represent optional features, particularly where the filters are employed in filtering other streams. Optionally if desired, a bleed valve (not shown) may be employed in the top housing so as to permit the discharge of entrapped air and the introduction of blood into the inlet 16.

Figure 5:
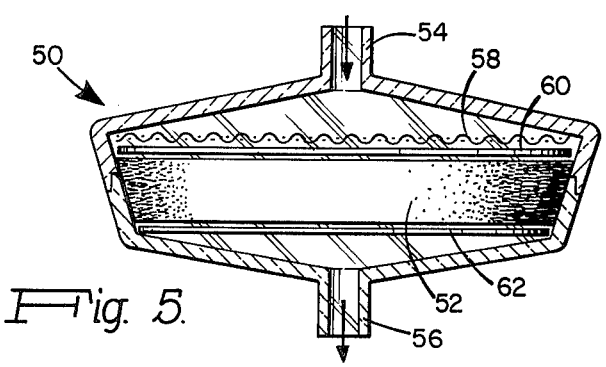
FIG. 5 is a schematic illustrative partially cross-sectional view of another embodiment of my filter.
Figure 4:
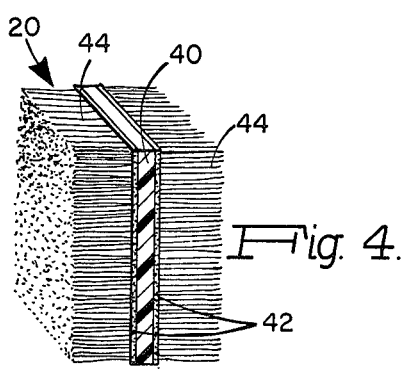
FIG. 4 is a schematic illustrative partially isomeric view of the flocked material employed in the filter element of FIG. 1.
Figure 6:
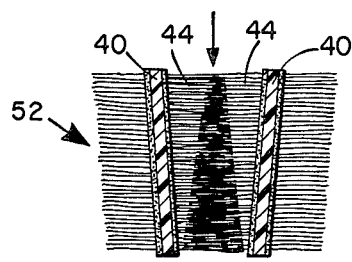
FIG. 6 is an illustrative schematic view of the position of the filter element in the filter of FIG. 5.

FIGS. 5 and 6 are directed to another embodiment of my filter, wherein there is shown a filter housing 52, a truncated conical-type which tapers inwardly toward the outlet. One disadvantage of the filter illustrated in FIGS. 1–4 is that, for the filtration of fluid streams, which contain a wide distribution of particle sizes; that is, contains very large particles, as well as very small particles, the leading edge portion of the helically coiled filter may become occluded by larger type particles. In order to overcome this disadvantage, the housing element and helically coiled filter may be modified as set forth in FIGS. 5 and 6 so as to permit the compressing of the helically wound filter core to provide for the leading edge of the helical filter core to be more open than the lower edge; that is, to create a gradient in the tightness of wind so as to permit particle removal through both gradient and depth filtration.

FIGS. 5 and 6 illustrate a modified filter 50 comprising a helically wound filter element 52, an inlet 54, an outlet 56, a screen 58, a flow distributor 60 and a filter 62. The helically wound filter element 52 is illustrated schematically in FIG. 6, and shows in exaggerated form at the tapered sides of the filter housing a restricting of the lower edge of the filter element, so as to provide for more overlapping of the fibrous flocked material, with less overlapping, or none at all if desired, at the upper part of the filter element 52 by providing for a gradient for the removal of a fluid stream containing large and small particles.

A blood filter of the type described in FIGS. 1–4 was constructed with 2 mm nylon, electrostatically flocked particles around a 3 mil mylar backing sheet, the flocked material being secured through a solvent-type urethane adhesive to the mylar sheet. A top and bottom flow distributor was employed on either side of the helically coiled filter element constructed of a sieve plate of 5 mil thickness mylar, and a post screen filter employed of about 140 mesh composed of nylon. The filter housing element was formed of a rigid polycarbonate resin at a diameter of approximately 2¼ inches, with the filter core chamber having a depth of about ¾ of an inch within the housing. The filter core element having the flocked nylon on both sides was approximately 100 cm in length and 1.2 cm in depth, the inlet and outlet being approximately ⅛ of an inch. The helically coiled flocked mylar sheet material was coiled about a solid, polycarbonate, ¼ inch central core, with the free end glued to the core, and wound helically around the core element.

Experimental, whole, outdated blood was passed through the filter configuration, and a rate of 120 ml per minute with gravity feed was measured. Observation of the filtered blood sample showed no change in hematocrit or induced hemolysis. Further, microscopic examination of the filtrate showed that the filtering removed all agglomeration seen in the blood initially, and no flock was seen in the filtrate.

In another test using the same or a similar filter, it has been found that the flocked filters of my invention exhibit a significantly smaller pressure drop than the Swank dacron wool filters of the prior art for the concentration of particles. My filters exhibited high flow rates at low pressure drops.

It is recognized that various changes and modifications in the particular materials and structure of my filter may be made by those skilled in the art without departing from the spirit and scope of my invention.

What I claim is:

1. A filter for a fluid stream which comprises in combination:
    (a) a filter housing adapted to contain a filter element;
    (b) a filter element disposed in the housing having an upstream end and a downstream end, and which element comprises a helically coiled strip of sheet material containing, on at least one surface thereof, a surface layer of fibrous flocked material, the sheet material wound into a helical coil of desired tightness within the housing, so as to prevent a multitude of channels through the flocked material to the fluid stream which passes axially through the coiled strip, the flocked material selected to remove particles from the fluid stream to be filtered, the helically coiled strip being wound such that an increasing gradient in the tightness of the wind from the upstream to the downstream ends provides for both gradient and depth filtration of the blood;
    (c) an inlet for the introduction of a fluid stream to be filtered into the housing; and
    (d) an outlet for removal of the filtered fluid stream from the housing.

2. The filter of claim 1 wherein the helically wound sheet material of the filter element contains a surface layer of fibrous flocked material secured on each side thereof to provide for overlapping of the fibrous flocked material of adjacent sides of the coil.

3. The filter of claim 1 wherein the inlet is disposed axially of the filter element to permit the introduction of the fluid stream to be filtered axially of the helically coiled filter element.

4. The filter of claim 1 wherein the sheet material comprises a thin flexible polymeric sheet material, and wherein the fibrous flocked material is secured to the surface of the sheet material by an adhesive.

5. The filter of claim 1 wherein the flocked material comprises finely divided fibers of an inert polymeric material.

6. The filter of claim 5 wherein the flocked fibrous material is selected from the group of polyester, polyamide, cellulose acetate, and combinations thereof.

7. The filter of claim 1 which includes a pair of funnel-like upper and lower housing elements to form the filter housing, and characterized by a centrally disposed upper inlet and a centrally disposed lower outlet.

8. The filter of claim 1 which includes a flat filter element disposed across the axial upstream cross-section of the helical coil filter element and having a pore size of about 50 to 200 microns.

9. The filter of claim 1 which includes a flat filter element disposed downstream of the coiled filter element to remove any fibrous flocked material detached from the coiled strip.

10. The filter of claim 1 which includes a flow distributor extending cross-sectionally across and upstream of the axis of the coil filter element, the flow distributor comprising a plurality of flow passages therein, and adapted to equalize the flow of the fluid stream to be filtered across the cross-sectional axial surface of the coil filter element.

11. The filter of claim 1 wherein the coil filter element includes a central solid core element, wherein the one end of the sheet material is secured to the core element and wound helically therearound to form the filter element.

12. The filter of claim 1 wherein the fibrous flocked material is uniformly distributed on the surface of the sheet material, and comprises fibers of not more than about 5 mm in length.

13. The filter of claim 1 wherein the filter housing tapers inwardly upstream to downstream of the axis of the filter element, and wherein the filter element is tapered along its axis from the upstream to the downstream to provide for both gradient and depth removal of particles from the stream to be filtered.

14. A filter for the filtration of blood, which filter comprises in combination:
 (a) a filter housing composed of upper and lower filter elements to form a filter housing in which a centrally disposed inlet for the introduction of blood to be filtered and a centrally disposed outlet for the removal of filtered blood;
 (b) a filter element disposed within the housing, and which filter element comprises a core element and wound about the core element a helically coiled strip of polymeric sheet material having adhesively secured to at least one surface thereof a fibrous flocked polymeric material having a fiber length of less than 5 mm, the sheet material wound into a helical coil of desired tightness so as to fit snugly within the filter housing, the helical coil disposed and axially aligned with the inlet and outlet of the housing to permit the passage of blood to be filtered by axial passage therethrough, the helically coiled strip being wound such that an increasing gradient in the tightness of the wind from the upstream to the downstream ends provides for both gradient and depth filtration of the blood;
 (c) a filter means upstream of the filter element to prefilter the blood, the filter means having pores of about 50 to 200 microns;
 (d) a flow distributor means upstream of the filter element and disposed to equalize the flow of the blood introduced into the inlet across the cross-section of the filter element; and
 (e) a screen filter element downstream of the filter element to remove detached fibrous flocked material from the filtered blood.

15. The filter of claim 14 wherein the flocked material is precision-cut and has a fiber length of about 1 to 3 mm and is compatible with the blood to be filtered.

16. The filter of claim 14 wherein the coiled strip of polymeric sheet material has fibrous flocked polymeric material secured to each side thereof, the flocked material of each side contacting and intermingling with the flocked material of the adjacent side.

17. A method of filtering blood, which method comprises:
 (a) passing the blood generally axially through a blood filter element which comprises a helically coiled strip of sheet material containing on at least one surface thereof a surface layer of a fibrous flocked material compatible with the blood to be filtered, and having a fiber length of less than about 5 mm, the sheet material wound into a helical coil of desired tightness to present a multitude of channels through the flocked material, the helically coiled strip being wound such that an increasing gradient in the tightness of the wind from the upstream to the downstream ends provides for both gradient and depth filtration of the blood; and
 (b) recovering the blood so filtered.

18. The method of claim 17 which includes prefiltering the blood prior to filtration with the filter element by passing the blood through a filter having pores of from about 50 to 200 microns.

19. The method of claim 17 which includes filtering the blood after passing through the filter element and prior to removing to remove displaced fibrous flocked material from the filtered blood.

20. The method of claim 17 wherein the sheet material has a fibrous flocked material on both sides of the sheet.

21. The method of claim 17 wherein the flocked material is a polymeric flocked material secured to a thin polymeric strip material, the flocked material having a fiber length of from about 1 to 3 mm.

22. The method of claim 17 wherein the length, diameter and flocked density of the fibrous flocked material is selected to remove the desired particles from the blood.

23. A filter for a fluid stream, which filter comprises in combination:
 (a) a filter housing adapted to contain a filter element and having an inlet at the one end for the introduction of a fluid stream to be filtered, and an outlet at the other end for the removal of the filtered stream; and
 (b) a filter element which comprises
  (i) a solid, flexible, helically coiled strip of sheet material,
  (ii) a layer of adhesive material on at least one surface of the sheet material, and
  (iii) fibrous particulate material adhesively secured to the adhesive layer to form a surface layer of the fibrous flocked material on the continuous surface, the filter element disposed in the housing as a helical coil of desired tightness to present a multitude of fibrous filter channels through the flocked material on the surface of the coil, the ends of the fibrous particulate material in contact with the adjacent surface of the sheet material or intermeshed with fibrous particulate material on said adjacent sheet material surface, the fibrous flocked material generally of uniform length and uniformly distributed on the surface of the sheet material, and which comprises fibers of not more than about 5 mm in length, the fibrous particulate material forming the flocked layer selected to remove particles from the stream to be filtered, the helical coil disposed to permit only axial flow of the fluid stream through the filter element as the stream passes from the inlet to the outlet of the housing.

24. The filter of claim 23 wherein the helically wound sheet material of the filter element contains a surface layer of fibrous flocked material secured on each side thereof, to provide for overlapping of the fibrous flocked material of adjacent sides of the coil.

25. The filter of claim 23 wherein the flocked fibrous material is selected from the group of polyester, polyamide, cellulose acetate, and combinations thereof.

26. The filter of claim 23 which includes a pair of funnel-like upper and lower housing elements to form the filter housing, and characterized by a centrally disposed upper inlet and a centrally disposed lower outlet.

27. The filter of claim 23 which includes a flat filter element disposed across the axial upstream cross-section of the helical coil filter element, and having a pore size of about 50 to 200 microns.

28. The filter of claim 23 which includes a flat filter element disposed downstream of the coiled filter element to remove any fibrous flock material detached from the coiled strip.

29. The filter of claim 23 which includes a flow distributor extending cross-sectionally across and upstream of the axis of the coil filter element, the flow distributor comprising a plurality of flow passages therein, and adapted to equalize the flow of the fluid stream to be filtered across the cross-sectional axial surface of the coil filter element.

30. The filter of claim 23 wherein the coil filter element includes a central solid core element, wherein the one end of the sheet material is secured to the core element and wound helically therearound to form the filter element.

31. The filter of claim 23 wherein the inlet is disposed axially of the filter element to permit the introduction of the fluid stream axially at the one end of the filter element.

32. The filter of claim 23 wherein the sheet material comprises a thin, flexible, polymeric sheet material having a thickness of from about 0.5 to 5 mils.

33. The filter of claim 23 wherein the filter includes:
(a) a flow distributor extending substantially across and upstream of the axis of the coiled filter element to distribute the flow of fluid introduced into the inlet across the cross-sectional area of the filter element; and
(b) a filter element disposed downstream of the axis of the filter element in the housing to remove any flock material detached from the filter element.

34. The filter of claim 33 wherein the flock material has a length of from about 1 to 3 mm.

35. A method of filtering blood to remove selected particles or biological constituents of the blood stream, which method comprises:
(a) passing the blood containing the particles to be removed, axially through a blood filter element which comprises
(i) a solid, flexible, helically coiled strip of sheet material,
(ii) a layer of adhesive material on at least one surface of the sheet material, and
(iii) fibrous particulate material adhesively secured to the adhesie layer to form a surface layer of the fibrous flocked material on the continuous surface, the fibrous flocked material compatible with the blood, the filter element disposed in the housing as a helical coil of desired tightness to present a multitude of fibrous filter channels through the flocked material on the surface of the coil, the ends of the fibrous particulate material in contact with the adjacent surface of the sheet material or intermeshed with fibrous particulate material on said adjacent sheet material surface, the fibrous flocked material generally of uniform length and uniformly distributed on the surface of the sheet material, and which comprises fibers of not more than about 5 mm in length, the fibrous particulate material forming the flocked layer selected to remove particles from the blood to be filtered, the helical coil disposed to permit only axial flow of the blood through the filter element as the blood passes from the inlet to the outlet of the housing; and
(b) recovering the blood so filtered.

36. The method of claim 35 which includes:
(a) distributing the blood to be filtered generally uniformly over the cross-sectional upstream area of the filter element; and
(b) filtering any detached flock material from the filtered blood downstream of the filter element, wherein the filter element comprises a thin, flexible, polymeric sheet material having inert fibrous flock material of a length of from about 1 to 3 mm secured to at least one side thereof by a layer of inert adhesive material.

37. The method of claim 35 which includes controlling the particle size of the material to be filtered from the blood by control of the length, diameter and density of the flock material and by the tightness of the helical winding of the filter element.

38. The method of claim 35 wherein the flexible sheet material includes a thin layer of adhesive material on each side of the sheet material and fibrous flock material is secured to the thin layer of adhesive material on each side of the sheet material, and which includes passing the blood generally axially to be filtered through the fibrous flocked material, the fibrous flocked material on one surface intermeshed with the fibrous flocked material on the adjacent and opposite surface of the sheet material.

39. The method of claim 35 wherein the fibrous flocked material comprises a polymeric flocked material secured to a thin polymeric flexible sheet material, the flocked material having an average fiber length of about 1 to 3 mm.

* * * * *